US009694217B2

(12) United States Patent
Goldstein et al.

(10) Patent No.: US 9,694,217 B2
(45) Date of Patent: Jul. 4, 2017

(54) POSITIVE AIR PRESSURE FACEMASK AND MULTI-STAGED FILTER SYSTEM THEREFOR

(71) Applicant: FAMASK, INC., Gaithersburg, MD (US)

(72) Inventors: Steven Goldstein, Gaithersburg, MD (US); Todd Grinspoon, Gaithersburg, MD (US); Wayne L. Thornton, Gaithersburg, MS (US)

(73) Assignee: FAMASK, INC., Gaithersburg, MD (US)

( * ) Notice: Subject to any disclaimer, the term of this patent is extended or adjusted under 35 U.S.C. 154(b) by 0 days.

(21) Appl. No.: 14/667,030

(22) Filed: Mar. 24, 2015

(65) Prior Publication Data

US 2016/0279450 A1 Sep. 29, 2016

(51) Int. Cl.

| | |
|---|---|
| ***A61M 16/00*** | (2006.01) |
| ***A62B 18/00*** | (2006.01) |
| ***A62B 7/10*** | (2006.01) |
| *A62B 18/02* | (2006.01) |

(52) U.S. Cl.

CPC .............. *A62B 18/006* (2013.01); *A62B 7/10* (2013.01); *A62B 18/02* (2013.01)

(58) Field of Classification Search

CPC ..... A62B 23/025; A62B 23/00; A62B 18/006; A62B 18/02; A62B 7/10; A62B 18/00; A62B 18/08; A61B 18/045; A41D 13/00; A42B 3/28

USPC ............ 128/205.25, 205.27–205.29, 206.17, 128/207.11

See application file for complete search history.

(56) References Cited

U.S. PATENT DOCUMENTS

| | | | | |
|---|---|---|---|---|
| 4,771,771 | A * | 9/1988 | Walther ................. | A62B 18/00 128/201.25 |
| 5,372,130 | A * | 12/1994 | Stern ...................... | A62B 18/08 128/205.25 |
| 5,957,131 | A | 9/1999 | Hutchinson et al. | |
| 6,412,945 | B1 | 7/2002 | Grove et al. | |
| 6,826,783 | B1 | 12/2004 | Grove et al. | |
| 6,854,464 | B2 | 2/2005 | Mukaiyama et al. | |
| 7,415,864 | B1 | 8/2008 | Israel et al. | |
| 7,464,705 | B2 | 12/2008 | Tanizawa et al. | |
| 7,584,751 | B1 | 9/2009 | Brooks, Jr. et al. | |
| 8,667,959 | B2 | 3/2014 | Tilley et al. | |
| 2007/0240716 | A1 | 10/2007 | Marx | |

(Continued)

*Primary Examiner* — Bradley Philips
*Assistant Examiner* — Victoria Leszczak
(74) *Attorney, Agent, or Firm* — Nath, Goldberg & Meyer; Joshua B. Goldberg; Scott H. Blackman

(57) ABSTRACT

Provided herein is a positive air pressure facemask, a multi-staged filter system for a positive air pressure face-mask, and exemplary methods for replacing the filter system of a positive air pressure facemask while the mask is in continuous use and actively worn by a user. The multi-staged filter system includes a front filter assembly having a plurality of removable filter layers for collecting debris and particulate matter on the exterior of the filter system, a blower assembly, and at least two staged filter inserts contained in the housing of the filter system. The staged filter inserts are easily replaceable and can be changed without requiring the user to remove the facemask or to be exposed to the ambient air.

3 Claims, 2 Drawing Sheets

(56) References Cited

U.S. PATENT DOCUMENTS

| | | | | |
|---|---|---|---|---|
| 2010/0108067 | A1 * | 5/2010 | Walker .................. | A62B 17/04<br>128/205.24 |
| 2012/0198804 | A1 * | 8/2012 | Kaiser ................ | B01D 46/0023<br>55/486 |
| 2013/0014751 | A1 | 1/2013 | Ausen | |
| 2013/0087151 | A1 | 4/2013 | Klockseth | |
| 2013/0092164 | A1 | 4/2013 | Curran et al. | |
| 2014/0216475 | A1 | 8/2014 | Blomberg et al. | |

* cited by examiner

POSITIVE AIR PRESSURE FACEMASK AND MULTI-STAGED FILTER SYSTEM THEREFOR

TECHNICAL FIELD

The present disclosure pertains to positive air pressure facemasks, a multi-staged filter system therefore, and exemplary methods for replacing the filter system of a positive air pressure facemask while in continuous use by a user.

BACKGROUND

Military personnel, law enforcement professionals, rescue personnel, medical and research professionals, and other groups of individuals (collectively referred to as "users") often wear respiratory protection devices, such as facemasks, for protection from environments containing harmful and potentially fatal airborne toxins and other hazardous materials. Such toxins and materials may appear in the form of gases, vapors, particulate matter, and the like.

One particular type of respiratory protection apparatus is a positive air pressure system. Positive air pressure devices are often used in environments where the ambient air is relatively oxygen rich and the filtering elements are effective in removing all contaminants from the ambient air before the air enters the mask. Positive air pressure systems typically have a forced positive pressure source, such as a fan or a blower element for directing the air flow through the filter element(s). These breathing assistance devices are commonly referred to as powered air purifying respirators (PAPR).

PAPRs provide a continual supply of positive air pressure to the mask portion of the respirator to maintain positive pressure therein. In operation, the blower element continuously supplies filtered air to the internal space of the mask portion of the PAPR for the user. Meanwhile, exhaled air is continuously expelled. The positive pressure prevents ambient air from entering the mask portion and by extension reduces if not eliminates the possibility of foreign matter entering an imperfectly fitting mask.

However, the conventional PAPR devices are not without drawbacks. For instance, most of the currently available PAPRs are not designed to permit rapid and easy replacement of used or "spent" filters. More importantly, currently available PAPR devices do not offer the ability to easy replace a spent filter while the facemask is in continuous use in a hazardous environment by the user.

In many cases, the filter portions of the PAPR systems employ threaded connectors. In order for the user to change out a spent filter, the user must unscrew and discard the used filter and quickly screw a replacement filter in its place. Regardless of how quick the user may be in exchanging filters, the user may nonetheless be exposed to the ambient air through the unfiltered filter connection during the exchange of the filter elements. Accordingly, the process for replacing a filter in the current PAPR systems may be time consuming and may also lead to increased exposure to contaminants.

As a result of their design configurations, the range of use for these PAPRs is often limited. Due to the potential exposure to ambient air during filter exchange, filter exchange is typically limited to areas where the ambient area is free of toxic or otherwise harmful contaminants, or "safe zones." In certain cases, these PAPR device may be required to be subjected to some level of decontamination prior to filter replacement in the safe zone.

An additional drawback is that conventional PAPR filters often tend to be bulky in size. Generally, the filters are relatively large cylindrically shaped cartridges. Depending on the positioning of the filters on the PAPR devices, the freedom of mobility of the user may be restricted or impaired, which consequently impacts how and in which environments the devices can be used.

Accordingly, there exists a long overdue need in the field for a filter system utilizing a positive air pressure that is quick and easy for the user to replace while actively using the positive air pressure system. More importantly, the filter system should permit the user to independently replace the used filters without assistance while remaining in the contaminated environment, and without the need for removing the facemask or without the risk of being exposed to the potentially hazardous ambient air.

SUMMARY

According to the present subject matter described herein, there is provided a positive air pressure facemask which comprises a mask portion; a first housing which contains a blower assembly, a printed circuit board (PCB), a power source, a switch, and a first filter insert; a second housing containing a second filter insert; a removable cap; and a front filter assembly comprising a plurality of filter layers. More importantly, the filter inserts are designed to be easily replaced from the housings even while the facemask is actively in use on a user. Similarly, the plurality of filter layers located on the front filter assembly may be individually peeled away from the filter assembly for removal therefrom. A preferred embodiment of the positive air pressure facemask further comprises a filter slot in each of the housings and an adjustment ring positioned on an exterior surface of the first housing containing the first filter insert, where the cap and the adjustment ring are each configured to cover one of the filter slots on the respective housings.

In another embodiment, the present subject matter provides a multi-staged filter system for a positive air pressure facemask. As described herein, an exemplary multi-staged filter system comprises a housing containing a first filter insert, a blower assembly, a second filter insert, two filter slots, a removable cap, and a front filter assembly comprising a plurality of removable filter layers. The multi-staged filter system may be configured to custom fit to any existing positive air pressure facemask. More importantly, the filter inserts are configured to be easily replaced from the housing by simply inserting a replacement filter into a respective filter slot, thereby ejecting the used filter from the slot as the new filter is positioned therein. Additionally, the plurality of removable filter layers may be individually peeled away from the front filter assembly as debris accumulates thereon while the facemask is being actively used by the user.

In another embodiment, the present subject matter provides a method for replacing a filter system in a positive air pressure facemask while the facemask is actively worn and in continuous use by the user. As described herein, an exemplary method for replacing the filter system comprises: rotating the cap to uncover the filter slot on the second housing; sliding a new filter insert into the filter slot thereby ejecting the installed filter insert from the filter slot; locking the cap back on the housing to cover the filter slot; moving the air adjustment ring along the exterior surface of the first housing in a direction toward the cap to uncover the filter slot; sliding another new filter insert into the filter slot thereby expelling the installed filter insert therefrom; and moving the air adjustment ring back along the exterior surface to cover the filter slot. Most importantly, the exemplary methods for replacing a filter system in a positive air pressure facemask as described herein are adapted to be performed while the facemask is actively worn and in continuous use by a user without removing the facemask from the user or exposing the portion of the user's face covered by the facemask to ambient air.

In short, the present subject matter provides a multi-tiered filter system for a positive air pressure facemask having filter inserts that are quick and easy to replace while the facemask is actively worn and in continuous use on a user. By providing a system of filter inserts that can be quickly and easily replaced, the multi-staged filter systems described herein offer the advantage of enabling a user to continue to wear the positive air pressure facemask for extended durations without the risk of exposure to the potentially hazardous ambient air.

DETAILED DESCRIPTION

The detailed descriptions of exemplary embodiments of the present subject matter are described herein. It is to be understood, however, that the present subject matter may be embodied in various forms and is not intended to be limited solely to the preferred embodiments discussed herein. The specific details elaborated herein are meant as a basis for the claims and should not be interpreted as limiting. Further, these details are intended to represent the basis for one of ordinary skill in the art to practice the present subject matter in any appropriate structure, system, or manner.

Figure 1:
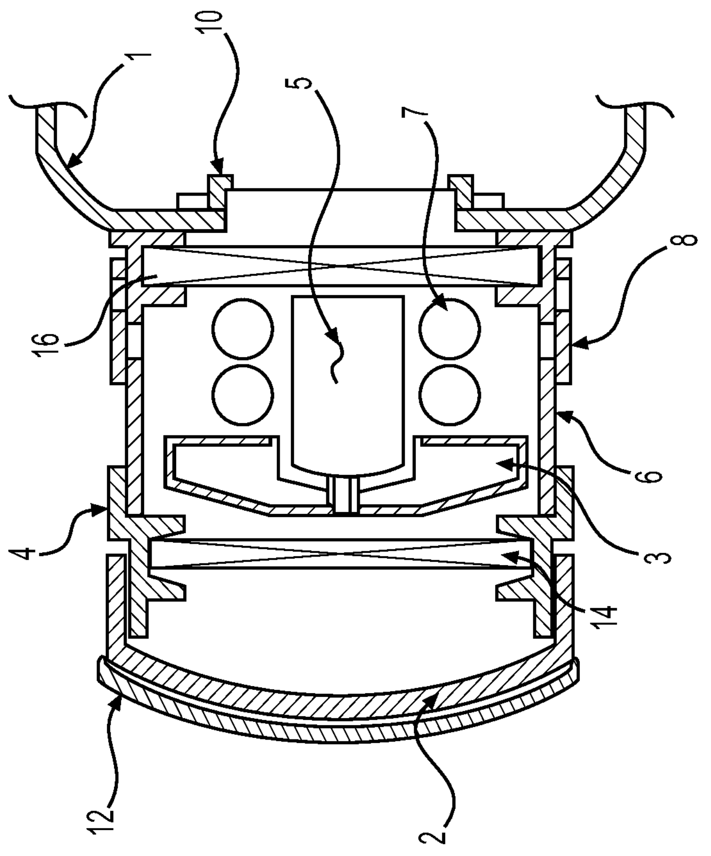
FIG. 1 is a cross-section of an exemplary multi-staged filter system.

Referring to FIG. 1, a cross-section of an exemplary multi-staged filter system is shown. The filter system comprises three filtering stages and is configured to securely attach to the mask portion (1) of a positive air pressure facemask via a locking ring (10). In one non-limiting embodiment, the mask portion (1) is secured between the locking ring (10) and the first housing (6). The mask portion (1) is not particularly limited in that it may comprise a partial facemask assembly, as known in the art, which covers only the user's mouth and nose. Alternatively, the mask portion (1) may comprise a full facemask assembly, as known in the art, such as a hood or helmet, which typically covers the user's entire face. In one preferred embodiment, the filter system is designed to extend outwards from the mask portion (1) by approximately 2¾ inches.

While FIG. 1 illustrates the filter system having first and second housing sections (6, 4), it is further provided that the first and second housing sections may be formed as a unitary structure. The housing(s) may be formed of plastic materials, particularly commodity resins and/or engineering resins. Commodity resins are desirable because they are typically inexpensive and easy to process. Engineering resins are also desirable for their mechanical and/or thermal properties. More specifically, engineering resins are generally high strength plastics that are often resistant to high temperatures, wear, and corrosive materials.

The first housing (6) is arranged to directly interface with the mask portion (1). In a preferred embodiment, the first housing (6) contains a blower assembly, a printed circuit board (PCB), a power source, and a first filter insert (16). The blower assembly typically comprises a fan blade (3) and a motor (5), which drives the fan (3), causing air to flow through the filter system to the mask portion (1). However, the use of other blower assemblies known in the art, which cause air to flow through the filter system, is contemplated.

In one non-limiting embodiment, the power source for the motor (5) comprises at least one battery. As shown in FIG. 1, there are four batteries (7) that are utilized to power the motor (5). The batteries may be rechargeable or non-rechargeable. Although the power source is not particularly limited, the total weight of the filter system is a consideration and it is desirable to minimize the weight without compromising the functionality of the system. For example, in one preferred embodiment, the multi-staged filter system, including the filter inserts, is designed to weigh about 245 grams, or less as needed.

The exterior of the first housing (6) includes an on/off switch, for supplying power to the blower assembly, and an air adjustment ring (8). The air adjustment ring (8) is located on the end of the first housing (6), which is adjacent to the mask portion (1). The air adjustment ring (8) is configured to slide axially along the exterior of the first housing (6) in a direction toward the second housing (4). The air adjustment ring (8) is further configured to lock on the first housing (6) in the axial position closest to the mask portion (1), which also covers first filter slot (190). Even though the air adjustment ring (8) may be axially locked on the exterior of the first housing (6), the air adjustment ring (8) is configured to be rotatable about the first housing (6) while in the locked position. Rotation of the air adjustment ring (8) allows the user to adjust the amount of air that enters the mask to maintain positive air pressure while simultaneously protecting the filter slot (190) from collecting debris therein from the ambient air.

The second housing (4) attaches to the first housing (6) at the open end, which is opposite to the end attached to the mask portion (1). A second filter insert (14) is contained within the second housing (4). In one preferred embodiment and as shown in FIG. 1, the first and second housings (6, 4) are arranged such that the blower assembly is axially positioned in between the first and second filter inserts (16, 14). In this regard, air flowing through the filter system first passes through the first filter insert (14) and is then motioned by the blower assembly through the second filter insert (16) before being delivered to the user through the mask portion (1).

Each of the first and second housings (6, 4) has a respective filter slot (190, 180) formed therein. Each filter slot (190, 180) further comprises a filter inlet (190*a*, 180*a*) and a filter outlet (190*b*, 180*b*). The filter slots can accommodate filter inserts having, for example, dimensions of 2½ inches wide by 3 inches long and with a thickness of ¼ inch. However, the present filter slots can be easily configured, modified, or adapted to accommodate any standard size filter as is generally available, known, currently in use, or contemplated for future use.

Figure 2:
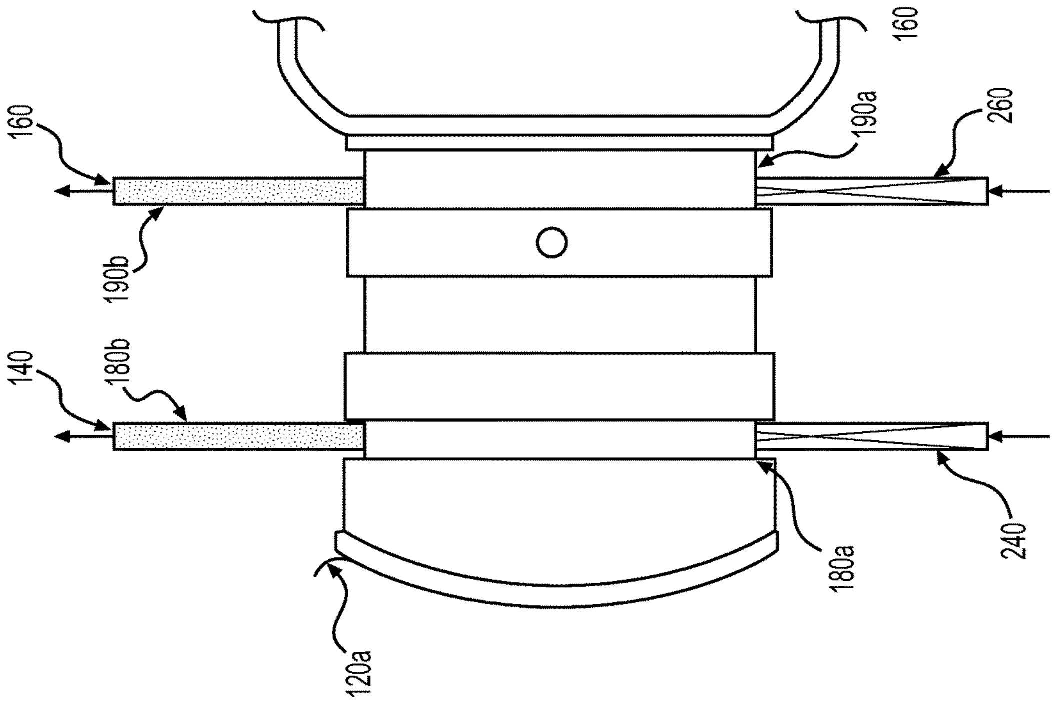
FIG. 2 is a side view of the multi-staged filter system.

Referring now to FIG. 2, when a filter insert becomes dirty and must be replaced, a new filter insert (240, 260) is inserted into the filter slot (180, 190) at the respective filter inlet (180*a*, 190*a*) of the used filter insert (140, 160). As the new filter (240, 260) enters the filter slot (180, 190), the used filter insert (140, 160) is expelled from the respective filter outlet (180*b*, 190*b*) of the filter slot (180, 190).

A removable cap (2) locks onto the free end of the second housing (4) via a friction fit between the cap (2) and the housing (4). When locked on the second housing (4), the cap (2) is configured to extend over and cover the filter slot (180).

A front filter assembly comprising a plurality of removable filter layers (12) is adapted to attach to the exterior surface of the cap (2). The number of filter layers (12) forming the plurality is not particularly limited, however, the filter layers should not impede air flow through the filter system. In one particular non-limiting embodiment, the optimal number of filter layers (12) comprising the plurality is six. In other embodiments, the number of filter layers can be any of 1, 2, 3, 4, 5, 6, 7, 8, 9, 10, or more as necessary. In order to attach to the cap (2), each individual filter layer (12) comprises an adhesive layer. In a preferred embodiment, the adhesive layer is formed around a perimeter of each respective filter layer (12).

Each of the plurality of filter layers (12) can be made of any suitable or customary material. In one non-limiting embodiment, each of the plurality of filter layers (12) can be formed of cloth or a woven material. In particular, these filter layers (12) form the initial filtering stage of the multi-staged filter system by collecting large debris or particulate material on the exterior surface of the filter system. In this regard, ambient air entering the filter system is first filtered through the plurality of filter layers (12) before passing through the cap (2) and the second housing (4) into the second filter insert (14). More importantly, the plurality of filter layers (12) is configured to be removable by peeling each individual layer away from and off of the front filter assembly. Accordingly, when the topmost filter layer of the front filter assembly has collected an amount of debris or particulate matter which impedes the air flow through the filter system of a facemask in active use, the user may easily and quickly remove the topmost layer from the front filter assembly by simply peeling it away without having to remove the mask portion or be exposed to the potentially hazardous ambient air.

Since the multi-staged filter system is designed to be used in combination with a variety of positive air pressure facemasks, there is no particular limitation regarding the type of filter material used in the filter inserts. The type of filter material used in the filter inserts will depend on the environmental application of the facemask. In other words, the type and the amount of airborne contaminant(s) will dictate which type of filter should optimally be used. Some examples of filter material types include, but are not limited to, carbon filters, electrostatic filters, HEPA filters, N95 filters, and P100 filters. In one embodiment, the type of filter material used can be changed while the present multi-staged filter system is in use due to a change in conditions or to maximize the effectiveness of the system. Such a change in filter material should optimally have minimal to no impact on the user. In another embodiment, the user may travel with a variety of different types of filters, so that s(he) can select the most appropriate filter as needed.

In another non-limiting embodiment, the present subject matter may be provided separately as a multi-staged filter system for a positive air pressure facemask. Similar to the positive air pressure facemask described herein, an exemplary multi-staged filter system comprises a housing containing a first filter insert (316), a blower assembly comprising a motor (305) and a fan (303), a second filter insert (314), two filter slots (390, 380), a removable cap (302), and a front filter assembly comprising a plurality of removable filter layers (312). Further, the multi-staged filter system may be configured to custom fit to any existing positive air pressure facemask.

Regardless of the specific facemask to which the multi-staged filter system is attached, the filter inserts (314, 316) are configured to be easily replaced from the housing by inserting a replacement filter (340, 360) into a respective filter slot (380, 390). As discussed above, when a replacement filter (340, 360) is inserted into the filter inlet (380*a*, 390*a*) of a respective filter slot (380, 390), the used filter is ejected from the filter outlet (380*b*, 390*b*) as the new filter (340, 360) is positioned therein. The simple configuration of the filter slots (380, 390) enables the user to easily and quickly replace the filter inserts of the filter system even while the facemask, to which the filter system is attached, is in active use.

One particular advantage of the multi-staged filter system for a positive air pressure facemask as described herein is the ability of the user to quickly and easily replace the filter inserts in an actively worn and in continuous use facemask without the need for removing the facemask or exposing the user to the ambient air.

One non-limiting exemplary method for replacing the filter system may be performed according to the following steps. First, the cap is removed to uncover the filter slot on the housing. The cap need not be entirely removed from the housing. The cap only needs to be moved far enough on the housing to expose the filter slot. Once the filter slot is exposed, a new filter insert is inserted into the filter inlet. As the new filter insert enters the filter slot, the used filter is ejected through the filter outlet. After the new filter insert is installed in the filter slot, the cap is locked back onto the housing thereby covering the filter slot. By locking the cap back on the housing, the filter slot is protected from collecting particulate matter therein from the ambient environment.

Next, the air adjustment ring is unlocked and axially moved along the exterior of the housing in the direction of the cap to uncover the filter slot. Once the filter slot is exposed, another new filter insert is placed into the filter inlet, thereby expelling the used filter insert from the filter slot through the filter outlet. After the new filter insert is installed in the filer slot, the air adjustment ring is moved back along the exterior surface of the housing over the filter slot and axially locked. The filter system replacement method may further comprise peeling a topmost filter layer from the plurality of filter layers away from the front filter assembly to remove the topmost layer whenever air flow through the front filter assembly is impeded by debris or particulates collected on the topmost filter layer. Further, the step of removing the topmost filter layer may be repeated a number of times until all of the filter layers are removed from the front filter assembly.

Although the subject matter has been described with reference to specific embodiments, this description is not intended to be construed in a limited sense. Various modifications of the disclosed embodiments, as well as alternative embodiments of the present subject matter will become apparent to persons skilled in the art upon the reference to the description of the subject matter presented herein. It is therefore contemplated that the appended claims will cover such modifications that fall within the scope of the present subject matter.

What is claimed:

1. A positive air pressure facemask comprising: a mask portion, a first housing containing a blower assembly, a printed circuit board (PCB), a power source, a switch, and a first filter insert, a second housing attached to the first housing and containing a second filter insert, a removable cap configured to lock onto the second housing, and a front filter assembly adapted to attach to the cap and comprising a plurality of filter layers configured to be removed by peeling each layer off of the front filter assembly while the facemask is in continuous use, and a filter slot in each of the first and second housings, wherein the cap is configured to cover the filter slot in the second housing when the cap is locked onto the second housing and, further comprising an air adjustment ring positioned on an exterior surface of the first housing on an end opposite the cap, the air adjustment ring configured to cover the filter slot in the first housing.

2. A positive air pressure facemask comprising: a mask portion, a first housing containing a blower assembly, a printed circuit board (PCB), a power source, a switch, and a first filter insert, a second housing attached to the first housing and containing a second filter insert, a removable cap configured to lock onto the second housing, and a front filter assembly adapted to attach to the cap and comprising a plurality of filter layers configured to be removed by peeling each layer off of the front filter assembly while the facemask is in continuous use, and a filter slot in each of the first and second housings, wherein each filter slot has a filter inlet and a filter outlet, and where each filter inlet is located adjacent to one end of a respective filter insert and each filter outlet is located adjacent to the other end of the respective filter insert.

3. The positive air pressure facemask of claim 2, wherein the respective filter insert is replaced by inserting a new filter insert into the filter inlet to thereby push the respective filter insert out of the filter outlet.

* * * * *